United States Patent
Katsuyama (12) 
(10) Patent No.: US 6,328,984 B1
(45) Date of Patent: Dec. 11, 2001

(54) SELECTIVE ANTIBACTERIAL COMPOSITION

(75) Inventor: Masako Katsuyama, Yokohama (JP)

(73) Assignee: Shiseido Co., Ltd. (JP)

( * ) Notice: Subject to any disclaimer, the term of this patent is extended or adjusted under 35 U.S.C. 154(b) by 0 days.

(21) Appl. No.: 09/556,627

(22) Filed: Apr. 21, 2000

(30) Foreign Application Priority Data

Apr. 22, 1999 (JP) .................................................. 11-115129
Apr. 22, 1999 (JP) .................................................. 11-115130

(51) Int. Cl.⁷ ....................................................... A61K 7/00
(52) U.S. Cl. .......................................... 424/401; 424/78.07
(58) Field of Search .................................. 424/401, 78.07

(56) References Cited

U.S. PATENT DOCUMENTS

| | | | |
|---|---|---|---|
| 4,220,665 | 9/1980 | Klein | 424/343 |
| 5,895,643 | 4/1999 | Hoppe et al. | 424/65 |
| 6,136,298 * | 10/2000 | Gaffar et al. | 424/49 |

FOREIGN PATENT DOCUMENTS

| | | | |
|---|---|---|---|
| 0 126/944 A | 12/1984 | (EP) . | |
| 0 297/310 A | 1/1989 | (EP) . | |
| 0 577/356 A | 1/1994 | (EP) . | |
| 2 713/086 | 6/1995 | (FR) | A61K/31/045 |
| XP002148392 | 1/1998 | (GB) | A61K/7/48 |
| 405221823 A * | 8/1993 | (JP) . | |
| 06305962 | 1/1994 | (JP) | A61K/31/415 |
| 07188046 A * | 7/1995 | (JP) . | |
| WO 95/15149 | 6/1995 | (WO) | A61K/7/48 |
| WO 98/00168 | 1/1998 | (WO) | A61K/45/06 |

OTHER PUBLICATIONS

Vaamonde, G., et al.; Inhibition of Staphylococcus–Aureus C–243 Growth in Laboratory Media with Water Activity adjusted using Less Usual Solutes; 1986 (Recd 1987); pp. 403–404, p. 404, right–hand column; figure 2.

* cited by examiner

*Primary Examiner*—Shelley A. Dodson
*Assistant Examiner*—Konata M. George
(74) *Attorney, Agent, or Firm*—Fei-Fei Chao; Venable, Baetjer, Howard & Civiletti (57) ABSTRACT

In order to provide a selective antibacterial composition which distinguishes a harmful *Staphylococcus aureus* that exists on diseased skin from a harmless *Staphylococcus epidermidis* that exists on a healthy skin, which shows sufficient ability to treat and prevent skin disease by limiting its antibacterial effect to the harmful *S.aureus* without affecting to the growth of the harmless *S.epidermidis,* and which is a external preparation for the treatment of atopic dermatitis especially, the selective antibacterial composition of the present invention contains a farnesol and/or a xylitol.

9 Claims, 5 Drawing Sheets

SELECTIVE ANTIBACTERIAL COMPOSITION

RELATED APPLICATIONS

This application claims from priority Japanese Patent Application No.11-115129 filed on Apr, 22, 1999 and Japanese Patent Application No.11-115130 filed on Apr. 22, 1999 which are incorporated herein by reference.

FIELD OF THE INVENTION

The present invention relates to a selective antibacterial composition and, in particular, to an improved antibacterial agent which is combined into an external preparation for application to the skin.

BACKGROUND OF THE INVENTION

In recent years, as the numbers of atopic dermatitis patients have increased, it has become known that the balance of the distribution of bacteria on the rough skin of an atopic dermatitis patient is disturbed. The harmless *Staphylococcus epidermidis* is the principal bacteria that always exists on the skin of healthy person. However, the harmful *Staphylococcus aureus* exists with *S.epidermidis* on the skin of the atopic dermatitis patient, such that the balance of the distribution of the bacteria on the skin deviates from the normal. It is also known that the symptom worsen with an increase of *S.aureus*. Therefore, conventionally, an external preparation for application to the skin for the treatment of atopic dermatitis contains an antibacterial agent to sterilize this harmful *S.aureus*.

Usually, however, when the antibacterial agent is applied to the skin of the atopic dermatitis patient, the harmless *S.epidermidis* is sterilized too. This result is not desirable, because the *S.epidermidis* on the skin prevents pathogenic microorganisms from fixing on to and invading the skin. Furthermore, because the distribution of bacteria on the skin becomes unnaturally skewed, the balance of the distribution of bacteria on the skin is disturbed all the more. These have negative effects on atopic dermatitis. For that reason, the conventional antibacterial treatment may not prove effective. Also, the numbers of harmless *S.epidermidis* decrease due to repetition of the conventional treatment. Accordingly, conventional antibacterial treatments for atopic dermatitis tend to gradually allow other harmful bacteria to easily fix on the skin and invade the skin.

SUMMARY OF THE INVENTION

The present invention is achieved in view of the foregoing prior art. An object of the present invention is to provide a selective antibacterial composition which distinguishes the harmful *Staphylococcus aureus* that exists on the skin of a cutaneous disease patient from the harmless *Staphylococcus epidermidis* that exists on healthy skin, which does not affect the growth and development of the harmless *S.epidermidis*, and which effectively treats and prevents cutaneous diseases, especially atopic dermatitis, by limiting its antibacterial action to only the harmful *S.aureus*.

The harmful *S.aureus* and the harmless *S.epidermidis* in the present invention are the bacteria that resembled extremely on the taxonomy. Generally, it is extremely difficult to sterilize one of both, or to inhibit the growth of one of both. However, as a result of diligent study by the inventor, the inventor discovered that the concentration of about 2000 ppm of farnesol inhibits the growth of only the harmful *S.aureus* and does not inhibit the growth of the harmless *S.epidermidis*. Furthermore, as a result of diligent study by the inventor, the inventor discovered that xylitol serves as a nutrient for only the harmless *S.epidermidis* and does not serve as the nutrient for the harmful *S.aureus*. Accordingly, the present invention was accomplished.

Namely, a selective antibacterial composition of the present invention contains a farnesol and/or a xylitol.

Also, in the present invention, it is preferable that the selective antibacterial composition contains 0.001 to 10 wt % of the farnesol.

Also, in the present invention, it is preferable that the selective antibacterial composition contains 0.01 to 30 wt % of the xylitol.

Also, in the present invention, it is preferable that the selective antibacterial composition is an external preparation for application to the skin.

Also, in the present invention, it is preferable that the selective antibacterial composition is an external preparation for the treatment of atopic dermatitis.

BEST MODE OF THE INVENTION

In the following section, the preferred embodiment for carrying out the present invention will be explained in detail.

A farnesol (3,7,11-trimethyl-2,6,10-dodecatrien-1-ol) used in the present invention is marketed as the synthetic perfume that has both an antibacterial effect and an aromatic floral odor with a fresh green note. The farnesol is sometimes contained in cosmetics. Also, the xylitol used in the present invention is used in a product designed to prevent tooth decay, because although it is sugar it does not serve as a nutrient for most bacteria.

The inventor discovered that the farnesol shows a strong antibacterial effect against the harmful *Staphylococcus aureus*, without comparably affecting the growth of the harmless *Staphylococcus epidermidis*. In the following section, the antibacterial effect that selectively applies to this *S.aureus* is described as "the selective antibacterial effect".

An amount of farnesol in the present invention is preferably 0.001 to 10 wt % in the whole composition, and even more preferably 0.01 to 5 wt % in the whole composition. It is not sometimes preferable to utilize less than 0.001 wt % antibacterial effect at such a low concentration. It is also not preferable to utilize more than 10 wt % of farnesol, because the selectivity of the antibacterial effect disappears above that concentration.

Furthermore, in the selective antibacterial composition of the present invention, the selective antibacterial effect improves when xylitol is used in addition to farnesol. The amount of xylitol used is preferably 0.01 to 30 wt %. More preferably, the amount of xylitol in the product is approximately 0.5 to 10 wt %. The selective antibacterial effect may not show improvement if the amount of the xylitol is less than 0.01 wt %, and may not show significant improvement if the amount of xylitol is more than 30 wt %.

The selective antibacterial composition of the present invention can be prepared in a variety of formulations such as an ointment agent, cream, milky lotion, lotion, gel, pomade, body oil, hair tonic, or spray. The selective antibacterial composition can be prepared in O/W style, or W/O style where the composition is an emulsion. Also, when the selective antibacterial composition is prepared in these formulations, both the components and the amount of each component can be adjusted within the appropriate range in accordance with conventional means. (The components and the amounts of each component are not limited to the working examples that are shown below.) The composition of the present invention can also contain an optional component(s) in optional amount(s) in proportions adjusted to the object of the formulation. It is also possible for the composition of the present invention to contain any of a number of known agents, for example: antiphlogistic agents, vitamins such as vitamin A, vitamin $B_6$, vitamin D, pantothenic acid and biotin; hormones such as adrenocorticotrophic hormone; and antihistaminic agents.

The selective antibacterial composition of the present invention is suitable for use as an external preparation for application to the skin, especially as an external preparation for the treatment of atopic dermatitis. However, the composition of the present invention can be used in the form of nasal drops or ear drops as well.

In the following section, several working examples are shown as embodiments of the present invention. However, the present invention is not limited by these working examples. The test results demonstrating with regard to the selective antibacterial effect of farnesol and xylitol are shown before the working examples of the selective antibacterial composition. All amounts are expressed as weight percent.

<Method>

The effect of a xylitol-free composition containing 0.2 wt % of farnesol in a milky lotion base was compared to the effect of the composition containing 5 wt % of xylitot in addition to the 0.2 wt % of farnesol by the following challenge test method.

The Challenge Test Method $10^6$ cfu/g of a sample bacteria was inoculated into each milky lotion. Then, the decrease in numbers of the bacteria was observed.

The sample strain is as follows.

<Sample strain>

*Staphylococcus aureus* (Harmful bacteria)
  *S.aureus* FDA209P : Type strain
  *S.aureus* Isolate: Isolate from an atopic dermatitis patient
*Staphylococcus epidermidis* (Harmless bacteria)
  *S.epidermidis* IF03762: Type strain
  *S.epidermidis* Isolate: Isolate from an atopic dermatitis patient <Inoculation Method of Strain>

A total of 4 patterns were inoculated as shown in Table 1. Namely, 2 patterns of single inoculation and 2 patterns of 2 strains mixed inoculation were carried out on the *Staphylococcus epidermidis* and *Staphylococcus aureus*.

TABLE 1

| Kind of inoculation and type of strain |
| --- |
| 1. Single inoculation of *Staphylococcus epidermidis* IF03762 (Type strain) |
| 2. Single inoculation of *Staphylococcus aureus* FDA209P (Type strain) |

TABLE 1-continued

| Kind of inoculation and type of strain |
| --- |
| 3. Mixed inoculation of *S.epidermidis* IF03762 (Type strain) and *S.aureus* FDA209P (Type strain) |
| 4. Mixed inoculation of *S.epidermidis* (Isolate from an atopic dermatitis patient) and *S.aureus* (Isolate from an atopic dermatitis patient) |

Figure 1:
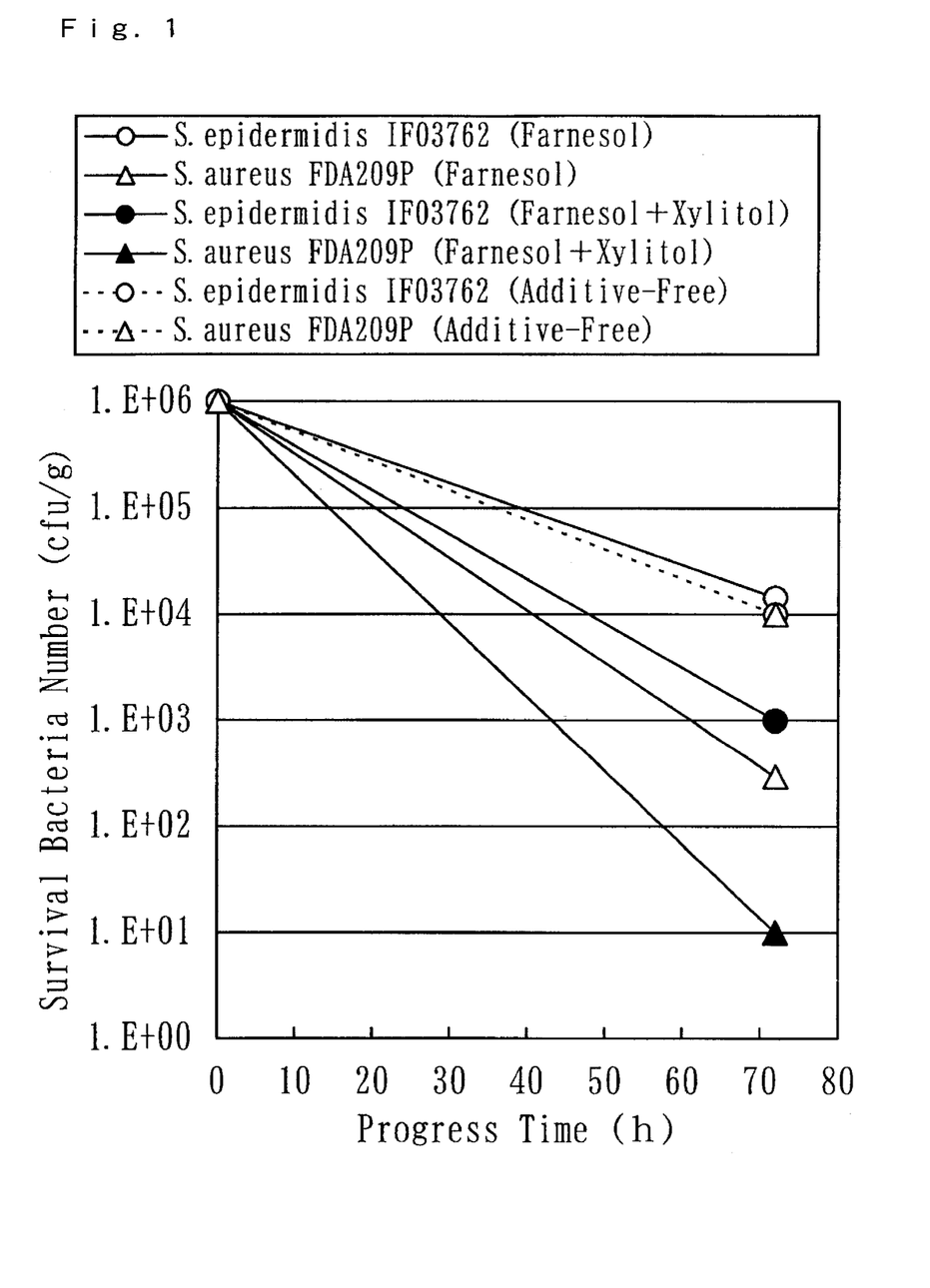
FIG. 1 shows the selective antibacterial effect of farnesol and xylitol using the Challenge test method (Use strain: *Staphylococcus epidermidis* IF03762 and *Staphylococcus aureus* FDA209P, Single inoculation).

FIG. 1 shows the results of applying the compositions to the single inoculation of the type strains using the challenge test method. It is shown that there is almost no change in the level of harmless *Staphylococcus epidermidis* IF03762 between the farnesol-free composition and the composition containing farnesol. On the other hand, it is shown that adding farnesol inhibits the growth of the harmful *Staphylococcus aureus* FDA209P. Accordingly, it is understood that farnesol shows an antibacterial effect selectively only against the harmful *S.aureus* FDA209P. FIG. 1 also shows that the selective antibacterial effect improves in the composition containing farnesol and xylitol.

Figure 2:
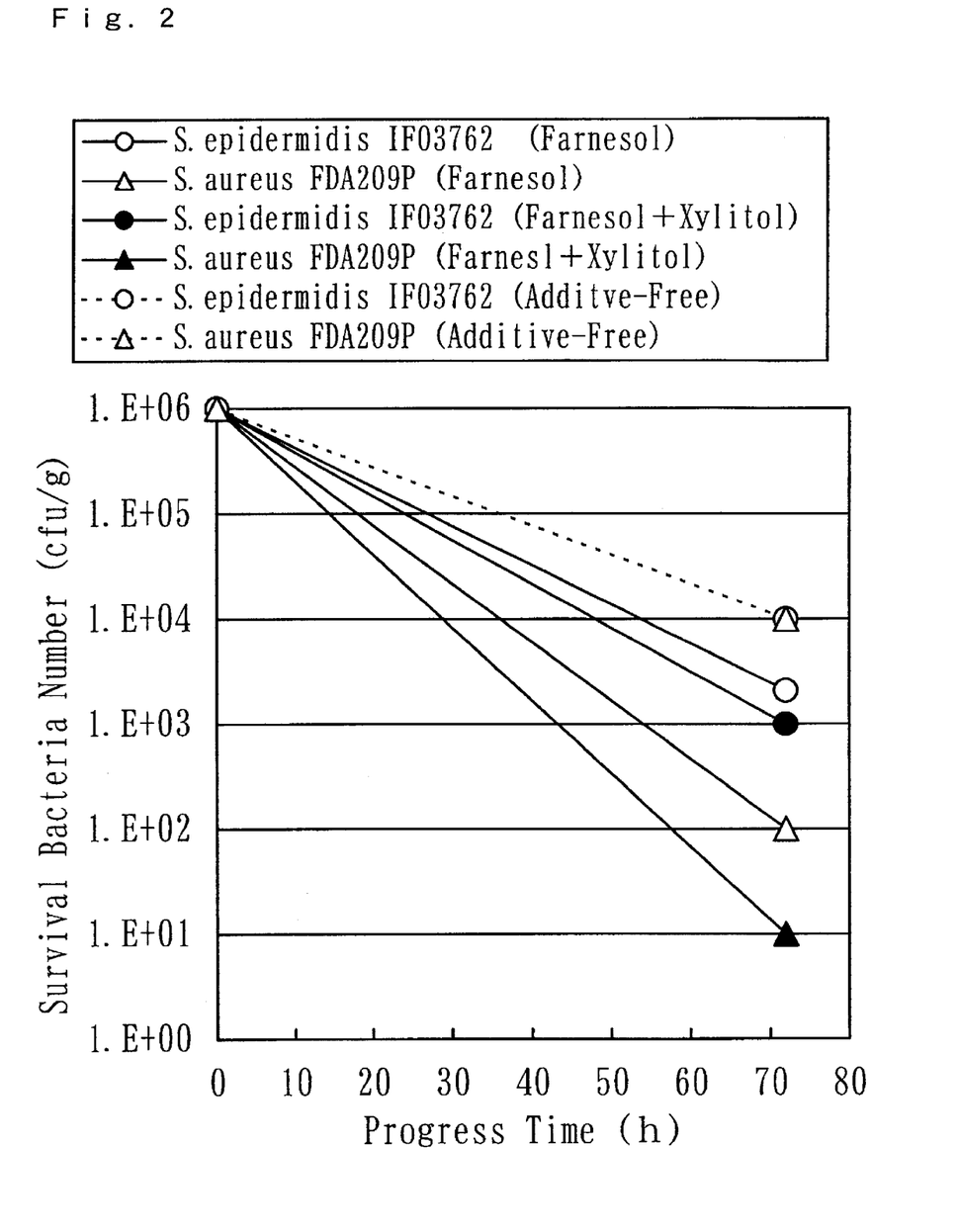
FIG. 2 shows the selective antibacterial effect of farnesol and xylitol using the Challenge test method (Use strain: *S.epidermidis* IF03762 and *S.aureus* FDA209P, Mixed inoculation).

FIG. 2 shows the results of applying the compositions to the mixed inoculations of the type strains using the challenge test method. It is shown that the composition containing farnesol has selective antibacterial effect against the harmful *Staphylococcus aureus* FDA209P which is much greater than its effect on the harmless *Staphylococcus epidermidis* IF03762. FIG. 2 also shows that the selective antibacterial effect is enhanced in the composition containing farnesol and xylitol.

Figure 3:
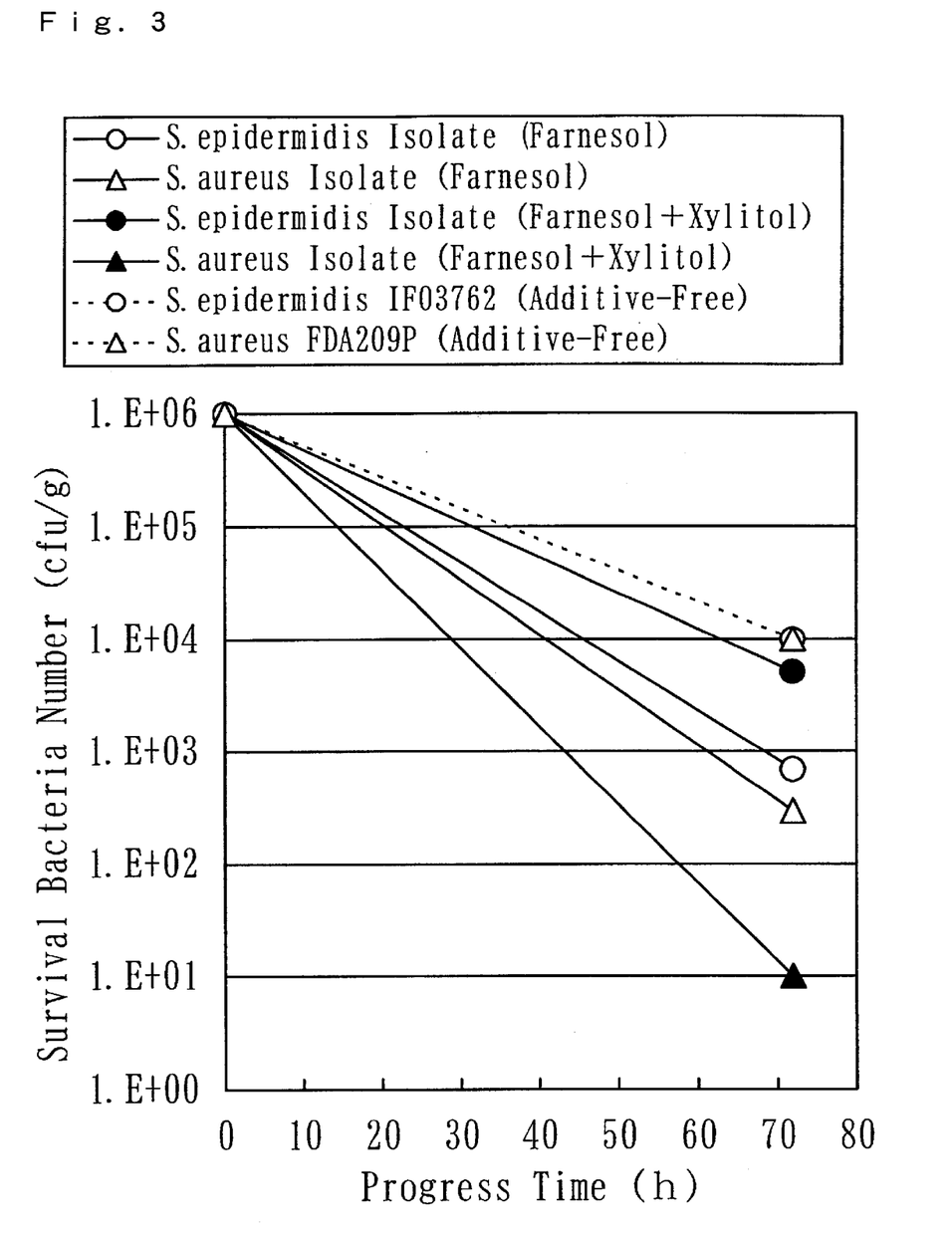
FIG. 3 shows the selective antibacterial effect of farnesol and xylitol using the Challenge test method (Use strain: *S.epidermidis* Isolate and *S.aureus* Isolate, Mixed inoculation).

FIG. 3 shows the results of applying the compositions to the mixed inoculation of the isolate from the atopic dermatitis patient using the challenge test method. Viewing the decreasing numbers of bacteria over time in the composition containing only farnesol, FIG. 3 shows that the harmful *S.aureus* isolate is inhibited to some extent, although there is relatively less distinction between the effect of the harmful *Staphylococcus aureus* isolate and the effect of the harmless *Staphylococcus epidermidis* isolate. FIG. 3 also shows, however, that the selective antibacterial effect is improved remarkably in the composition containing farnesol and xylitol.

The effects of the antibacterial compositions in the imitation sebum cream of Table 2, formulated to resemble human sebum, were evaluated using the challenge test method by applying them to the above-mentioned harmless *Staphylococcus epidermidis* isolate and the above-mentioned harmful *Staphylococcus aureus* isolate, which had been isolated from the same atopic dermatitis patient.

TABLE 2

| Imitation sebum cream(*) | Comp. Ex. 1 | Test Ex. 1 | Test Ex. 2 |
| --- | --- | --- | --- |
| A. Water phase | | | |
| Ion-exchanged water | 69.4 | 69.2 | 64.2 |
| Preservatives assistant | | | |
| Ethanol | 1.3 | 1.3 | 1.3 |
| Drug Xylitol | — | — | 5.0 |
| B. Oil phase | | | |
| Sebum | | | |
| Glyceryl tristearate | 10.7 | 10.7 | 10.7 |
| Stearic acid | 5.3 | 5.3 | 5.3 |
| Squalene | 3.2 | 3.2 | 3.2 |
| Stearyl stearate | 6.7 | 6.7 | 6.7 |
| Cholesterol | 0.8 | 0.8 | 0.8 |

TABLE 2-continued

| Imitation sebum cream(*) | Comp. Ex. 1 | Test Ex. 1 | Test Ex. 2 |
|---|---|---|---|
| Surfactant | | | |
| Emalex GWIS(*1) | 1.3 | 1.3 | 1.3 |
| Sunsoft 8004(*2) | 1.3 | 1.3 | 1.3 |
| Drug Farnesol | — | 0.2 | 0.2 |

*: Imitation sebum cream is adjusted to pH5.7 with PBS (—) [the phosphoric acid buffer solution does not include $Ca^{2+}$ and $Mg^{2+}$] (The same is true for the imitation sebum creams listed below).
*1: Trade name: Emalex GWIS (Polyoxyethylene glyceryl isostearate, manufactured by Japan Emulsion Inc.; The Emalex GWIS listed below is the same.)
*2: Trade name: Sunsoft 8004 (Glyceryl monostearate, lipophilic, manufactured by Taiyo Chemical Industry Inc.; The Sunsoft 8004 listed below is the same.)

<Manufacturing Method>

The drugs were added to the water phase (part A) and to the oil phase (part B). Each part was heated at 70° C. and dissolved completely. The A phase was then added to the B phase, and the combination was emulsified by an emulsifier. The emulsion was cooled by a heat exchanger, and the cream was obtained.

Figure 4:
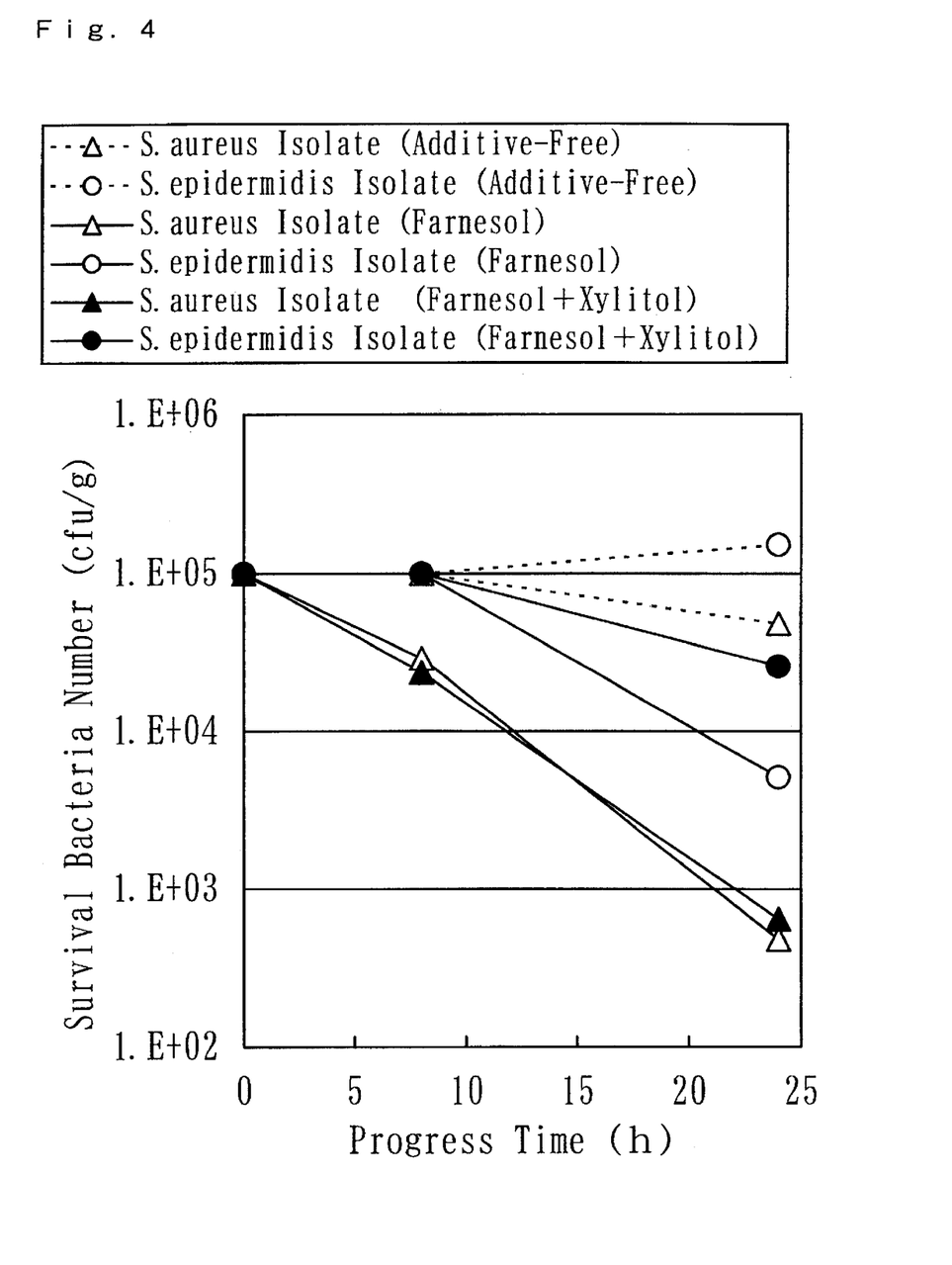
FIG. 4 shows the selective antibacterial effect of farnesol and xylitol in imitation sebum cream (Use strain: *S.epidermidis* Isolate and *S.aureus* Isolate, Single inoculation).

FIG. 4 shows the results of applying this imitation sebum cream to the single inoculation.

FIG. 4 shows that even the composition containing only farnesol shows a selective antibacterial effect. However, FIG. 4 also shows that the selective antibacterial effect is greatly enhanced in the cream of containing farnesol and xylitol.

Figure 5:
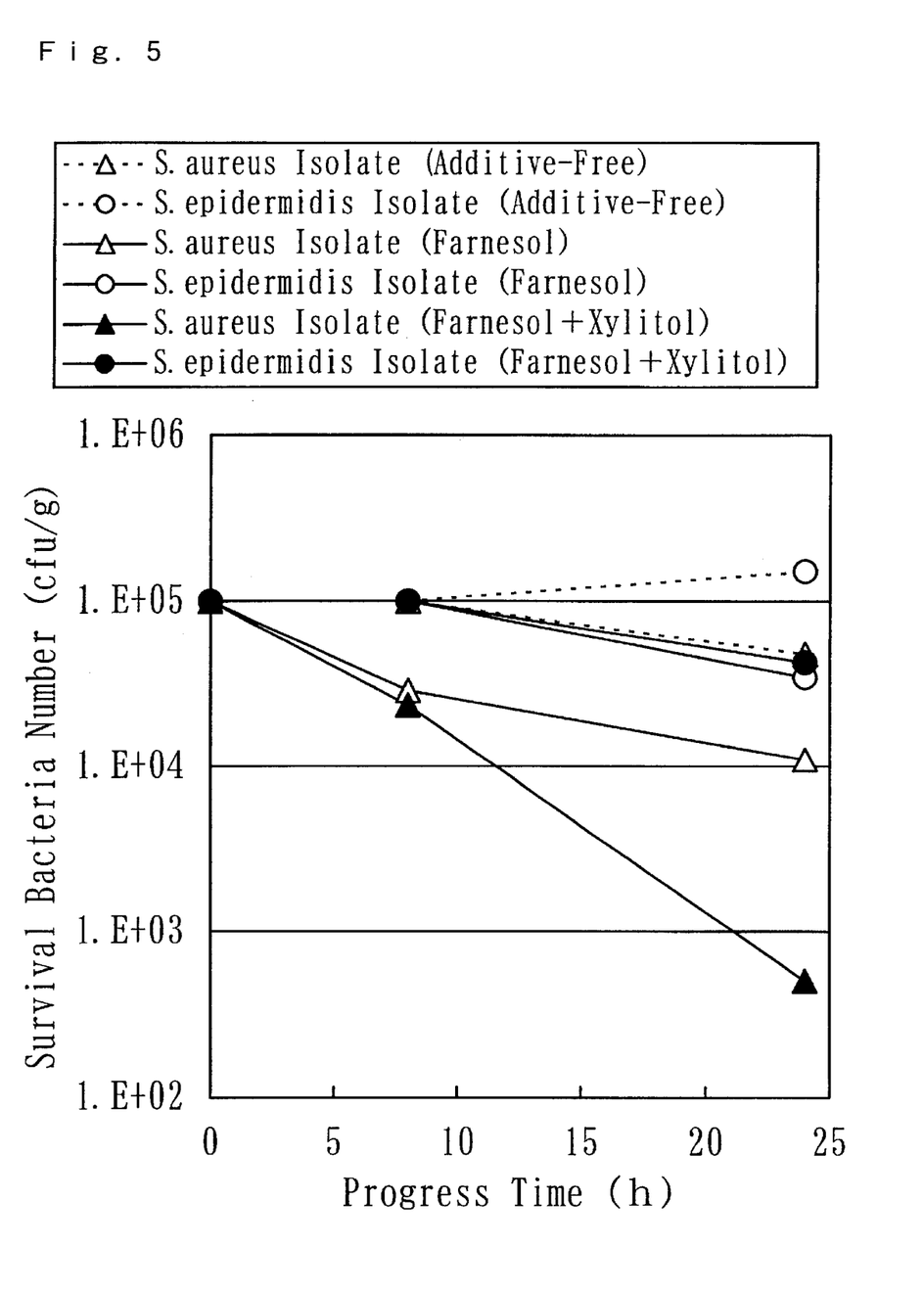
FIG. 5 shows the selective antibacterial effect of farnesol and xylitol in imitation sebum cream (Use strain: *S.epidermidis* Isolate and *S.aureus* Isolate, Mixed inoculation).

FIG. 5 shows the results of applying the imitation sebum cream to the mixed inoculation.

In the mixed inoculation, although the pattern of decrease differs from that of the single inoculation, even the composition containing only farnesol shows some selective antibacterial effect. FIG. 5 also shows that the selective antibacterial effect greatly improves in the composition containing xylitol and farnesol FIG. 4 and FIG. 5 show that the selective antibacterial effect is distinctly improved in composition containing farnesol and xylitol, although the selective antibacterial effect is obtained in compositions containing only farnesol. Accordingly, the aforementioned result led to the following table (Table 3) showing the effects of farnesol and xylitol.

TABLE 3

| | Staphylococcus epidermidis (Harmless bacteria) | Staphylococcus aureus (Harmful bacteria) |
|---|---|---|
| Farnesol | Antibacterial effect: Less | Antibacterial effect: Greater |
| Xylitol | Nutrient | Unnutrient |
| | ↓ | ↓ |
| | Proliferation easy | Growth inhibiting |

Amount of Farnesol

Next, the proper amount of farnesol to use the in the selective antibacterial composition was studied. The above-mentioned test was carried out using the imitation sebum cream in Table 4, applied single inoculations of *Staphylococcus aureus* FDA209P (Type strain) and *Staphylococcus epidermidis* IF03762 (Type strain). The selective antibacterial effect was again confirmed.

The evaluation standard is shown below.
<Evaluation Standard>
 ◎ The selective antibacterial effect was clearly improved in comparison with Comparative Example 2.
 ○ The selective antibacterial effect was improved in comparison with Comparative Example 2.
 Δ The selective antibacterial effect was barely confirmed in comparison with Comparative Example 2.
 X Unable to confirm the improvement of selective antibacterial effect in comparison with Comparative Example 2.

The results are shown in Table 4 and 5.

TABLE 4

| Imitation sebum cream | Comp. Ex.2 | Test Ex.3 | Test Ex.4 | Test Ex.5 | Test Ex.6 |
|---|---|---|---|---|---|
| A. Water phase | | | | | |
| Ion-exchanged water | Bal. | Bal. | Bal. | Bal. | Bal. |
| Ethanol | 1.3 | 1.3 | 1.3 | 1.3 | 1.3 |
| Xylitol | — | 5.0 | 5.0 | 5.0 | 5.0 |
| B. Oil phase | | | | | |
| Glyceryl tristearate | 10.7 | 10.7 | 10.7 | 10.7 | 10.7 |
| Stearic acid | 5.3 | 5.3 | 5.3 | 5.3 | 5.3 |
| Squalene | 3.2 | 3.2 | 3.2 | 3.2 | 3.2 |
| Stearyl stearate | 6.7 | 6.7 | 6.7 | 6.7 | 6.7 |
| Cholesterol | 0.8 | 0.8 | 0.8 | 0.8 | 0.8 |
| Emalex GWIS | 1.3 | 1.3 | 1.3 | 1.3 | 1.3 |
| Sunsoft 8004 | 1.3 | 1.3 | 1.3 | 1.3 | 1.3 |
| Farnesol | — | — | 0.0001 | 0.001 | 0.01 |
| Evaluation | — | Δ | Δ | ○ | ◎ |

TABLE 5

| Imitation sebum cream | Test Ex.7 | Test Ex.8 | Test Ex.9 |
|---|---|---|---|
| A. Water phase | | | |
| Ion-exchanged water | Balance | Balance | Balance |
| Ethanol | 1.3 | 1.3 | 1.3 |
| Xylitol | 5.0 | 5.0 | 5.0 |
| B. Oil phase | | | |
| Glyceryl tristearate | 10.7 | 10.7 | 10.7 |
| Stearic acid | 3.2 | 3.2 | 3.2 |
| Stearyl stearate | 6.7 | 6.7 | 6.7 |
| Cholesterol | 0.8 | 0.8 | 0.8 |
| Emalex GWIS | 1.3 | 1.3 | 1.3 |
| Sunsoft 8004 | 1.3 | 1.3 | 1.3 |
| Farnesol | 0.1 | 5.0 | 10.0 |
| Evaluation | ◎ | ◎ | ○ |

In Table 4 and Table 5, it is shown that the amount of farnesol in the selective antibacterial composition of the present invention is preferably about 0.001 to 10 wt %. However, it is not preferred to use more than 10 wt % of farnesol, because one cannot expect improvement of the antibacterial effect. Furthermore, it is not preferable because the selectivity of the antibacterial effect disappears above that concentration.

Amount of Xylitol

Next, the proper amount of xylitol to use in the selective antibacterial composition was studied. *Staphylococcus aureus* FDA209P (Type strain) and *Staphylococcus epidermidis* IF03762 (Type strain) were used as the samples. The above-mentioned test was carried out using the imitation sebum cream of the composition in Table 6 applied to single inoculations. Again, the selective antibacterial effect was confirmed.

The evaluation standard is shown below.
<Evaluation Standard>
 ◎ The selective antibacterial effect was clearly improved in comparison with Comparative Example 2.
 ○ The selective antibacterial effect was improved in comparison with Comparative Example 2.
 Δ The selective antibacterial effect was barely confirmed in comparison with Comparative Example 2.
 X Unable to confirm the improvement of selective antibacterial effect in comparison with Comparative Example 2.

The results are shown in Table 6.

TABLE 6

| Imitation sebum cream | Comp. Ex. 2 | Test Ex. 10 | Test Ex. 11 | Test Ex. 12 | Test Ex. 13 | Test Ex. 14 | Test Ex. 15 |
|---|---|---|---|---|---|---|---|
| A. Water phase | | | | | | | |
| Ion-exchanged water | Bal. | Bal. | Bal. | Bal. | Bal. | Bal. | Bal. |
| Ethanol | 1.3 | 1.3 | 1.3 | 1.3 | 1.3 | 1.3 | 1.3 |
| Xylitol | — | — | 0.001 | 0.01 | 0.5 | 10.0 | 30.0 |
| B. Oil phase | | | | | | | |
| Glyceryl tristearate | 10.7 | 10.7 | 10.7 | 10.7 | 10.7 | 10.7 | 10.7 |
| Stearic acid | 5.3 | 5.3 | 5.3 | 5.3 | 5.3 | 5.3 | 5.3 |
| Squalene | 3.2 | 3.2 | 3.2 | 3.2 | 3.2 | 3.2 | 3.2 |
| Stearyl stearate | 6.7 | 6.7 | 6.7 | 6.7 | 6.7 | 6.7 | 6.7 |
| Cholesterol | 0.8 | 0.8 | 0.8 | 0.8 | 0.8 | 0.8 | 0.8 |
| Emalex GWIS | 1.3 | 1.3 | 1.3 | 1.3 | 1.3 | 1.3 | 1.3 |
| Sunsoft 8004 | 1.3 | 1.3 | 1.3 | 1.3 | 1.3 | 1.3 | 1.3 |
| Farnesol | — | 0.1 | 0.1 | 0.1 | 0.1 | 0.1 | 0.1 |
| Evaluation | — | Δ | Δ | ○ | ⊚ | ⊚ | ○ |

In Table 6, it is shown that the amount of the xylitol in the selective antibacterial composition of the present invention is preferably approximately 0.01 to 30 wt %. However, it is not preferred or economic to use more than 30 wt %, because the great improvement of the selective antibacterial effect may not be obtained.

Next, several working examples of the external preparation for application to the skin for the treatment of atopic dermatitis are shown as embodiments of the selective antibacterial composition of the present invention. These working examples do not limit the present invention.

WORKING EXAMPLE 1
Cream

| | Components | Amount(wt %) |
|---|---|---|
| A. | Cetanol | 0.5 |
| | Petrolatum | 2.0 |
| | Squalane | 7.0 |
| | Glyceryl monostearate, selfemulsifying | 2.5 |
| | Polyoxyethylene (20) sorbitan monostearate | 1.5 |
| | Pantothenyl ethyle ether | 0.5 |
| | Farnesol | 0.2 |
| | Jojoba oil | 5.0 |
| B. | Propylene glycol | 5.0 |
| | Glycerin | 5.0 |
| | Beegum(Montmorillonite) | 5.0 |
| | Xylitol | 5.0 |
| | Purified water | balance |

Manufacturing Method

Each of A (Oil phase) and B (Water phase) were heated to 70° C. and dissolved completely. A was emulsified with the emulsifier in combination with B. The emulsion was cooled with the heat exchanger, and the cream was obtained.

WORKING EXAMPLE 2
Cream

| | Components | Amount(wt %) |
|---|---|---|
| A. | Stearic acid | 10.0 |
| | Stearyl alcohol | 4.0 |
| | Butyl stearate | 8.0 |
| | Glyceryl monostearate | 2.0 |
| | Vitamin E acetate | 0.5 |

-continued

| | Components | Amount(wt %) |
|---|---|---|
| | Vitamin A palmitate | 0.1 |
| | Macademia nut oil | 1.0 |
| | Farnesol | 0.5 |
| | Perfume | 0.4 |
| | Antiseptic | q.s. |
| B. | Glycerin | 4.0 |
| | 1,2-pentanediol | 3.0 |
| | Potassium hydroxide | 0.4 |
| | Magnesium ascorbate phoshate | 0.1 |
| | Xylitol | 3.0 |
| | Trisodium edetate | 0.05 |
| | Purified water | balance |

Manufacturing Method

Each of the water phase (part A) and the oil phase (part B) was heated to 70° C. and dissolved completely. Part A was added to part B and was emulsified with the emulsifier. The emulsion was cooled with the heat exchanger, and the cream was obtained.

WORKING EXAMPLE 3
Cream

| | Components | Amount(wt %) |
|---|---|---|
| A. | Cetanol | 4.0 |
| | Petrolatum | 7.0 |
| | Isopropyl myristate | 8.0 |
| | Squalane | 15.0 |
| | Glyceryl monostearate | 2.2 |
| | Polyoxyethylene (20) sorbitan monostearate | 2.8 |
| | Vitamin E nicotinate | 2.0 |
| | Farnesol | 0.2 |
| | Perfume | 0.3 |
| | Antioxidants | q.s. |
| | Antiseptics | q.s. |
| B. | Glycerin | 5.0 |
| | Dipropylene glycol | 4.0 |
| | Sodium pyrrolidonecarboxylate | 1.0 |
| | Xylitol | 12.0 |
| | Disodium edetate | 0.01 |
| | Purified water | balance |

Manufacturing Method

The cream was obtained in conformity with Working Example 1.

WORKING EXAMPLE 4
Milky Lotion

|   | Components | Amount(wt %) |
|---|---|---|
| A. | Squalane | 5.0 |
|   | Oleyl oleate | 3.0 |
|   | Petrolatum | 2.0 |
|   | Sorbitan sesquioleate | 0.8 |
|   | Polyoxyethylene (20) oleyl ether | 1.2 |
|   | Farnesol | 0.1 |
|   | Evening primrose oil | 0.5 |
|   | Perfume | 0.3 |
|   | Antiseptics | q.s. |
| B. | 1,3-butylene glycol | 4.5 |
|   | Balm mint extract | 1.5 |
|   | Ethanol | 3.0 |
|   | Carboxyvinyl polymer | 0.2 |
|   | Potassium hydroxide | 0.1 |
|   | Xylitol | 7.0 |
|   | Sodium hexametaphosphate | 0.05 |
|   | Purified water | balance |

Manufacturing Method

The milky lotion was obtained in conformity with Working Example 1.

WORKING EXAMPLE 5
Foundation

|   | Components | Amount(wt %) |
|---|---|---|
| A. | Cetanol | 3.5 |
|   | Hydrogenated lanolin | 4.0 |
|   | Jojoba oil | 5.0 |
|   | Petrolatum | 2.0 |
|   | Squalane | 6.0 |
|   | Glyceryl monostearate | 2.5 |
|   | Polyoxyethylene (60) hydrogenated castor oil | 1.5 |
|   | Polyoxyethylene (20) cetyl ether | 1.0 |
|   | Pyridoxine palmitate | 0.1 |
|   | Farnesol | 1.0 |
|   | Antiseptics | q.s. |
|   | Perfume | 0.3 |
| B. | Propylene glycol | 10.0 |
|   | Mixed powder | 12.0 |
|   | Xylitol | 4.0 |
|   | Trisodium edetate | 0.2 |
|   | Purified water | balance |

Manufacturing Method

The foundation was obtained in conformity with Working Example 1.

WORKING EXAMPLE 6
Lotion

|   | Components | Amount(wt %) |
|---|---|---|
| A. | Ethanol | 5.0 |
|   | Polyoxyethylene oleyl alcohol ether | 2.0 |
|   | 2-ethylhexyl-p-dimethylaminobenzoate | 0.18 |
|   | Farnesol | 0.005 |
|   | Antiseptics | q.s. |
|   | Perfume | 0.05 |

-continued

|   | Components | Amount(wt %) |
|---|---|---|
| B. | 1,3-Butylene glycol | 9.5 |
|   | Sodium pyrrolidonecarboxylate | 0.5 |
|   | Nicotinamide | 0.3 |
|   | Glycerin | 2.0 |
|   | Hydroxypropyl-β-cyclodextrin | 1.0 |
|   | Citric acid | 0.05 |
|   | Sodium citrate | 0.1 |
|   | Xylitol | 8.0 |
|   | Purified water | balance |

Manufacturing Method

The alcohol phase (A) was added to the water phase (B) and was solubilized, and the lotion was obtained.

These Working Examples of the present invention showed efficacy for, the treatment and the prevention of atopic dermatitis, as external preparations for application to the skin.

A selective antibacterial composition of the present invention contains a farnesol and/or a xylitol. Further, the selective antibacterial composition distinguishes the harmful *Staphylococcus aureus* that exists on the skin of atopic dermatitis patient from the harmless *Staphylococcus epidermidis* that exist on healthy skin, and has an antibacterial effect to harmful *S.aureus* without affecting the growth of harmless *S.epidermidis*. Accordingly, this selective antibacterial composition shows a sufficient effect for the treatment and the prevention of cutaneous disease, especially atopic dermatitis.

What is claimed is:

1. A composition comprising a farnesol and a xylitol, wherein said composition has a selective antibacterial effect, and wherein said composition is an external preparation for skin.

2. The composition according to claim 1, wherein said composition comprises 0.001 to 10 wt % of the farnesol.

3. The composition according to claim 1, wherein said composition comprises 0.01% to 30 wt % of the xylitol.

4. The composition according to claim 1, wherein said composition is an external preparation for treatment of atopic dermatitis.

5. A composition comprising a farnesol and a xylitol, wherein said composition has a selective antibacterial effect, and wherein said composition is a preparation for a nasal drop.

6. A composition comprising a farnesol and a xylitol, wherein said composition has a selective antibacterial effect, and wherein said composition is a preparation for an ear drop.

7. The composition according to claim 1, wherein said composition inhibits a growth of *Staphylococcus aureus* without affecting a growth of *Staphylococcus epidermidis*.

8. The composition according to claim 5, wherein said composition inhibits a growth of *Staphylococcus aureus* without affecting a growth of *Staphylococcus epidermidis*.

9. The composition according to claim 6, wherein said composition inhibits a growth of *Staphylococcus aureus* without affecting a growth of *Staphylococcus epidermidis*.

* * * * *